(12) United States Patent  
Platt

(10) Patent No.: US 7,927,330 B2
(45) Date of Patent: Apr. 19, 2011

(54) MULTI-PORT SIDE-FIRE COAGULATOR

(75) Inventor: Robert C. Platt, Laguna Niguel, CA (US)

(73) Assignee: Covidien AG, Neuhausen am Rheinfall (CH)

(*) Notice: Subject to any disclaimer, the term of this patent is extended or adjusted under 35 U.S.C. 154(b) by 444 days.

(21) Appl. No.: 12/047,864

(22) Filed: Mar. 13, 2008

(65) Prior Publication Data

US 2008/0215045 A1    Sep. 4, 2008

Related U.S. Application Data

(63) Continuation of application No. 10/919,614, filed on Aug. 17, 2004.

(51) Int. Cl.
*A61B 18/18* (2006.01)
*A61F 7/00* (2006.01)

(52) U.S. Cl. ............... 606/41; 606/45; 606/47; 606/48; 606/49; 606/50; 607/107

(58) Field of Classification Search .............. 604/34, 604/40, 41, 49, 20–26, 501, 506–508, 93.01, 604/264, 523; 606/41, 45, 47–50; 607/107
See application file for complete search history.

(56) References Cited

U.S. PATENT DOCUMENTS

| 2,708,933 A | 5/1955 | August |
| 2,828,747 A | 4/1958 | August |
| 3,434,476 A | 3/1969 | Shaw et al. |
| 3,569,661 A | 3/1971 | Ebeling |
| 3,595,239 A | 7/1971 | Petersen |
| 3,692,973 A | 9/1972 | Oku et al. |
| 3,699,967 A | 10/1972 | Anderson |
| 3,832,513 A | 8/1974 | Klasson |
| 3,838,242 A | 9/1974 | Goucher |
| 3,903,891 A | 9/1975 | Brayshaw |
| 3,970,088 A | 7/1976 | Morrison |
| 3,987,795 A | 10/1976 | Morrison |
| 3,991,764 A | 11/1976 | Incropera et al. |
| 4,014,343 A | 3/1977 | Esty |
| 4,019,925 A | 4/1977 | Nenno et al. |
| 4,040,426 A | 8/1977 | Morrison, Jr. |
| 4,041,952 A | 8/1977 | Morrison, Jr. et al. |

(Continued)

FOREIGN PATENT DOCUMENTS

DE    3710489    11/1987

(Continued)

OTHER PUBLICATIONS

Grund et al., "Endoscopic Argon Plasma . . . Flexible Endoscopy"; Endoscopic Surgery and Allied Technologies, No. 1, vol. 2, pp. 42-46 (Feb. 1994).

(Continued)

*Primary Examiner* — Patricia M Bianco
*Assistant Examiner* — Nihir Patel

(57) ABSTRACT

An electrosurgical apparatus for coagulating tissue used in combination with an endoscope which includes an elongated flexible tube having a plurality of side-ports located therethrough. The tube extends through a working channel of the endoscope and an ionizable gas is supplied to the tube at or near the proximal end of the tube. A diffusing member directs the ionizable gas from the proximal end of the tube through each of the side-ports towards the tissue. An electrode is used for ionizing the gas prior to the gas exiting the side-ports.

10 Claims, 8 Drawing Sheets

U.S. PATENT DOCUMENTS

| | | | |
|---|---|---|---|
| 4,043,342 A | 8/1977 | Morrison, Jr. |
| 4,057,064 A | 11/1977 | Morrison, Jr. et al. |
| 4,060,088 A | 11/1977 | Morrison, Jr. et al. |
| 4,209,018 A | 6/1980 | Meinke et al. |
| 4,242,562 A | 12/1980 | Karinsky et al. |
| 4,311,145 A | 1/1982 | Esty et al. |
| 4,492,231 A | 1/1985 | Auth |
| 4,492,845 A | 1/1985 | Kljuchko et al. |
| 4,545,375 A | 10/1985 | Cline |
| 4,577,637 A | 3/1986 | Mueller, Jr. |
| 4,601,701 A | 7/1986 | Mueller, Jr. |
| 4,665,906 A | 5/1987 | Jervis |
| 4,708,137 A | 11/1987 | Tsukagoshi |
| 4,711,238 A | 12/1987 | Cunningham |
| 4,728,322 A | 3/1988 | Walker et al. |
| 4,732,556 A | 3/1988 | Chiang et al. |
| 4,753,223 A | 6/1988 | Bremer |
| 4,781,175 A | 11/1988 | McGreevy et al. |
| 4,817,613 A | 4/1989 | Jaraczewski et al. |
| 4,822,557 A | 4/1989 | Suzuki et al. |
| 4,864,824 A | 9/1989 | Gabriel et al. |
| 4,890,610 A | 1/1990 | Kirwan, Sr. et al. |
| 4,901,719 A | 2/1990 | Trenconsky et al. |
| 4,901,720 A | 2/1990 | Bertrand |
| 4,931,047 A | 6/1990 | Broadwin et al. |
| 4,955,863 A | 9/1990 | Walker et al. |
| 5,015,227 A | 5/1991 | Broadwin et al. |
| 5,041,110 A | 8/1991 | Fleenor |
| 5,061,268 A | 10/1991 | Fleenor |
| 5,061,768 A | 10/1991 | Kishimoto et al. |
| 5,067,957 A | 11/1991 | Jervis |
| 5,088,997 A | 2/1992 | Delahuerga et al. |
| 5,098,430 A | 3/1992 | Fleenor |
| 5,108,389 A | 4/1992 | Cosmescu |
| RE33,925 E | 5/1992 | Bales et al. |
| 5,122,138 A | 6/1992 | Manwaring |
| D330,253 S | 10/1992 | Burek |
| 5,152,762 A | 10/1992 | McElhenney |
| 5,160,334 A | 11/1992 | Billings et al. |
| 5,163,935 A | 11/1992 | Black et al. |
| 5,195,959 A | 3/1993 | Smith |
| 5,195,968 A | 3/1993 | Lundquist et al. |
| 5,207,675 A | 5/1993 | Canady |
| 5,217,457 A | 6/1993 | Delahuerga et al. |
| 5,234,457 A | 8/1993 | Andersen |
| 5,242,438 A | 9/1993 | Saadatmonesh et al. |
| 5,244,462 A | 9/1993 | Delahuerga et al. |
| 5,248,311 A | 9/1993 | Black et al. |
| 5,256,138 A | 10/1993 | Burek et al. |
| RE34,432 E | 11/1993 | Bertrand |
| 5,292,320 A | 3/1994 | Brown et al. |
| 5,306,238 A | 4/1994 | Fleenor |
| 5,324,283 A | 6/1994 | Heckele |
| 5,330,469 A | 7/1994 | Fleenor |
| RE34,780 E | 11/1994 | Trenconsky et al. |
| 5,366,456 A | 11/1994 | Rink et al. |
| 5,370,649 A | 12/1994 | Gardetto et al. |
| 5,380,317 A | 1/1995 | Everett et al. |
| 5,389,390 A | 2/1995 | Kross |
| 5,476,461 A | 12/1995 | Cho et al. |
| 5,496,308 A | 3/1996 | Brown et al. |
| 5,537,499 A | 7/1996 | Brekke |
| 5,620,439 A | 4/1997 | Abela et al. |
| 5,653,689 A | 8/1997 | Buelna et al. |
| 5,662,621 A | 9/1997 | Lafontaine |
| 5,669,904 A | 9/1997 | Platt, Jr. et al. |
| 5,669,907 A | 9/1997 | Platt, Jr. et al. |
| 5,688,261 A | 11/1997 | Amirkhanion et al. |
| 5,700,260 A | 12/1997 | Cho et al. |
| 5,716,365 A | 2/1998 | Goicoechea et al. |
| 5,720,745 A * | 2/1998 | Farin et al. ............ 606/49 |
| 5,782,860 A | 7/1998 | Epstein et al. |
| 5,782,896 A | 7/1998 | Chen et al. |
| 5,797,920 A | 8/1998 | Kim |
| 5,800,500 A | 9/1998 | Spelman et al. |
| 5,800,516 A | 9/1998 | Fine et al. |
| 5,821,664 A | 10/1998 | Shahinpoor |
| 5,836,944 A | 11/1998 | Cosmescu |
| 5,848,986 A | 12/1998 | Lundquist et al. |
| 5,855,475 A | 1/1999 | Fujio et al. |
| 5,908,402 A | 6/1999 | Blythe |
| 5,964,714 A | 10/1999 | Lafontaine |
| 5,972,416 A | 10/1999 | Reimels et al. |
| 6,039,736 A | 3/2000 | Platt |
| 6,080,183 A | 6/2000 | Tsugita et al. |
| 6,102,940 A | 8/2000 | Robichon et al. |
| 6,117,167 A | 9/2000 | Goicoechea et al. |
| 6,139,519 A | 10/2000 | Blythe |
| 6,149,648 A | 11/2000 | Cosmescu |
| 6,197,026 B1 | 3/2001 | Farin et al. |
| 6,213,999 B1 | 4/2001 | Platt, Jr. et al. |
| 6,264,650 B1 | 7/2001 | Hovda et al. |
| 6,348,051 B1 | 2/2002 | Farein et al. |
| 6,458,125 B1 | 10/2002 | Cosmescu |
| 6,475,217 B1 | 11/2002 | Platt |
| 6,558,383 B2 | 5/2003 | Cunningham et al. |
| 6,602,249 B1 | 8/2003 | Stoddard |
| 6,616,660 B1 * | 9/2003 | Platt ............... 606/49 |
| 6,666,865 B2 | 12/2003 | Platt |
| 6,852,112 B2 * | 2/2005 | Platt ............... 606/49 |
| 6,911,029 B2 | 6/2005 | Platt |
| 7,033,353 B2 | 4/2006 | Stoddard |
| 2001/0018587 A1 | 8/2001 | Yamamoto |
| 2002/0022838 A1 | 2/2002 | Cunningham et al. |
| 2003/0093073 A1 | 5/2003 | Platt |
| 2003/0144654 A1 | 7/2003 | Hilal |
| 2004/0088029 A1 | 5/2004 | Yamamoto |
| 2004/0167512 A1 | 8/2004 | Stoddard |
| 2004/0167617 A1 | 8/2004 | Voellmicke et al. |
| 2005/0015086 A1 | 1/2005 | Platt |
| 2005/0070894 A1 | 3/2005 | McClurken |
| 2005/0171528 A1 | 8/2005 | Sartor |
| 2005/0197658 A1 | 9/2005 | Platt |
| 2006/0052771 A1 | 3/2006 | Sartor |
| 2006/0052772 A1 | 3/2006 | Sartor et al. |
| 2006/0052774 A1 | 3/2006 | Garrison et al. |
| 2006/0200122 A1 | 9/2006 | Sartor et al. |
| 2007/0208337 A1 | 9/2007 | Podhajsky et al. |
| 2007/0213709 A1 | 9/2007 | Podhajsky |

FOREIGN PATENT DOCUMENTS

| | | |
|---|---|---|
| DE | 4139029 | 6/1993 |
| DE | 4326037 | 2/1995 |
| DE | 9117019 | 4/1995 |
| DE | 195 37 897 A1 | 3/1997 |
| DE | 9117299 | 4/2000 |
| DE | 19848784 | 5/2000 |
| DE | 29724247 | 8/2000 |
| EP | 0 447 121 A2 | 9/1991 |
| EP | 0 612 535 A1 | 8/1994 |
| EP | 0956827 A1 | 11/1999 |
| EP | 1 090 599 A | 4/2001 |
| EP | 127 551 A1 | 8/2001 |
| EP | 1 199 037 A2 | 4/2002 |
| EP | 1 199 038 A2 | 4/2002 |
| EP | 1 199 037 A3 | 7/2003 |
| EP | 1 199 038 A3 | 7/2003 |
| EP | 1 323 384 A2 | 7/2003 |
| EP | 1 323 384 A3 | 1/2004 |
| EP | 1 561 430 | 8/2005 |
| EP | 1 561 430 A1 | 8/2005 |
| EP | 1 570 798 A2 | 9/2005 |
| EP | 1 595 507 A2 | 11/2005 |
| FR | 1340509 | 9/1963 |
| GB | 1014995 | 12/1965 |
| JP | 61-159953 | 7/1986 |
| SU | 1438745 | 11/1988 |
| WO | WO 91/13593 | 9/1991 |
| WO | WO 93/03678 | 3/1993 |
| WO | WO 96/27337 | 9/1996 |
| WO | WO 99/15091 | 4/1999 |
| WO | WO 01/62333 | 8/2001 |
| WO | WO 02/058762 A2 | 8/2002 |
| WO | WO 02/058762 A3 | 8/2002 |
| WO | WO 2005/016142 | 2/2005 |

OTHER PUBLICATIONS

Farin et al., Technology of Argon Plasma . . . Endoscopic Applications; Endoscopic Surgery and Allied Technologies, No. 1, vol. 2, pp. 71-77 (Feb. 1994).
Brand et al., "Electrosurgical Debulking of Ovarian Cancer: A New Technique Using the Argon Beam Coagulator"; Gynecologic Oncology 39 pp. 115-118 (1990).
Hernandez et al., "A Controlled Study of the Argon Beam Coagultor for Partial Nephrectomy"; The Journal of Urology, vol. 143, May (J. Urol. 143: pp. 1062-1065, 1990).
Ward et al., "A Significant New Contribution to Radical Head and Neck Surgery"; Arch Otolaryngology, Head and Neck Surg., vol. 115 pp. 921-923 (Aug. 1989).
Mark H. Mellow, "The Role of Endoscopic Laser Therapy in Gastrointestinal Neoplasms"; Advanced Therapeutic Endoscopy, pp. 17-21, 1990.
Silverstein et al., "Thermal Coagulation Therapy for Upper Gatrointestinal Bleeding"; Advanced Therapeutic Endoscopy, pp. 79-84, 1990.
Waye et al., "Endoscopic Treatment Options"; Techniques in Therapeutic Endoscopy, pp. 1.7-1.15, 1987.
European Search Report EP 01 10 2843.8-2305, dated May 15, 2001.
International Search Report PCT/US98/19284, dated Jan. 14, 1999.
European Search Report EP 05 00 2257, dated Jun. 1, 2005.
European Search Report EP 06 01 9572 dated Nov. 21, 2006.
European Search Report EP 07 00 4356.
European Search Report EP 07 00 4659.

* cited by examiner

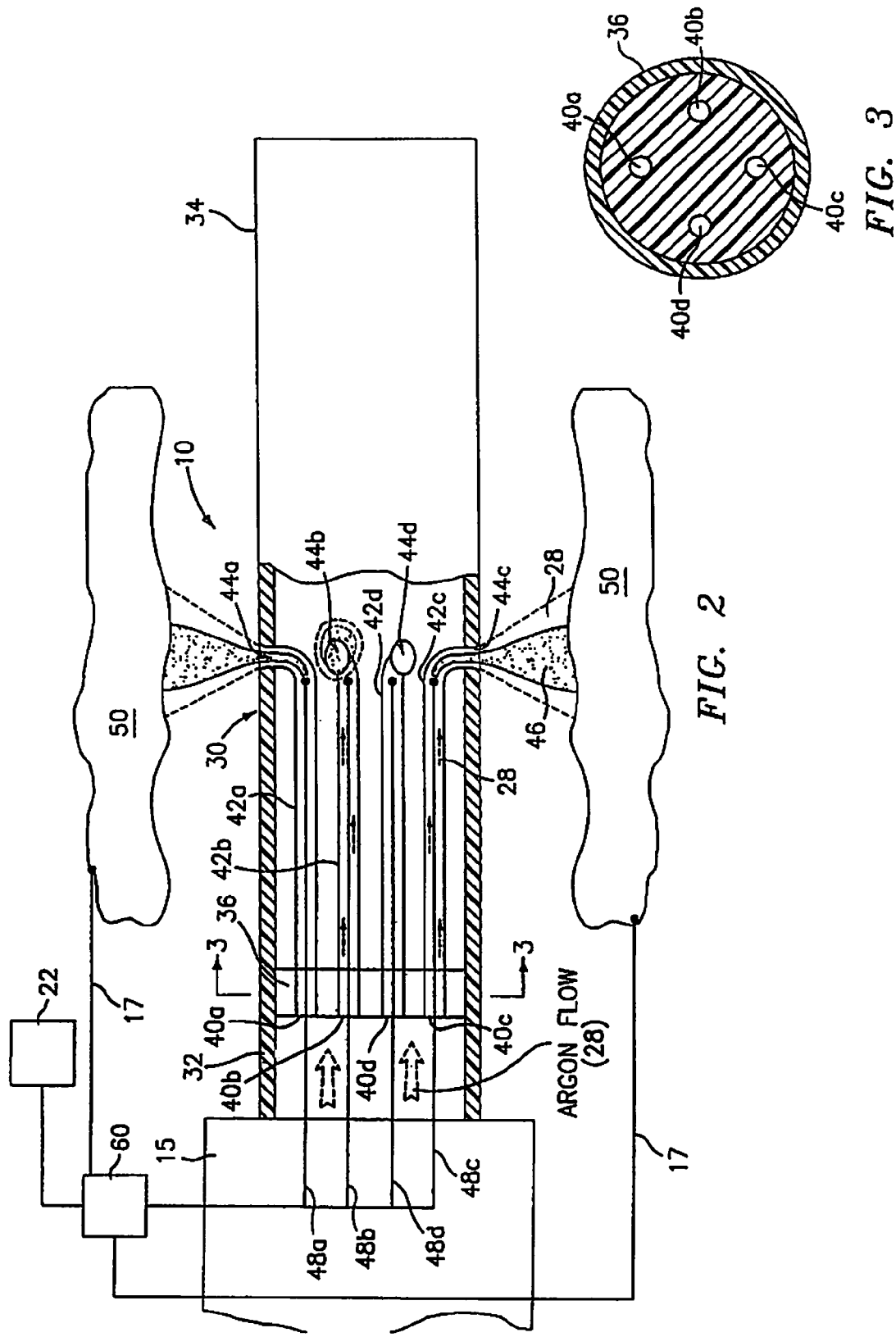

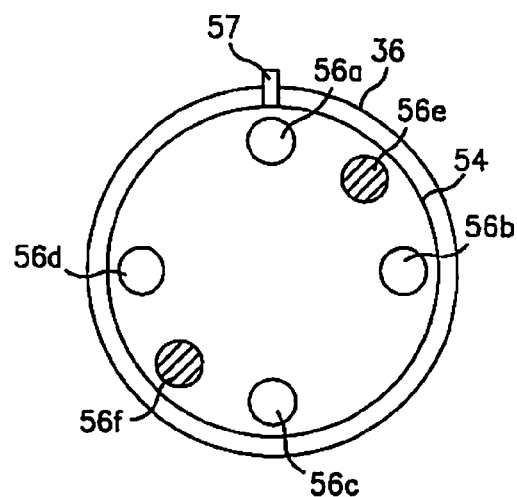
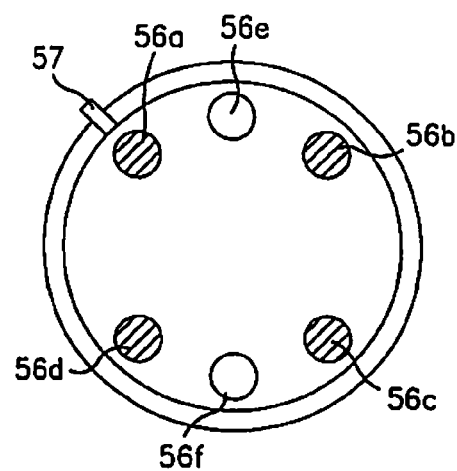
FIG. 5A                FIG. 5B
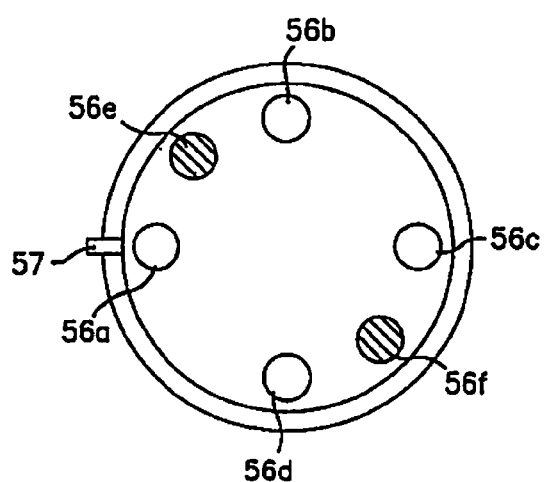
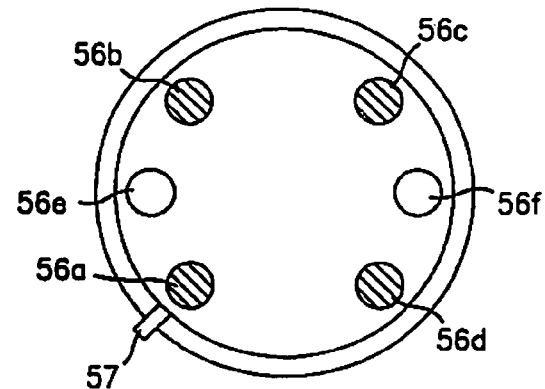
FIG. 5C                FIG. 5D

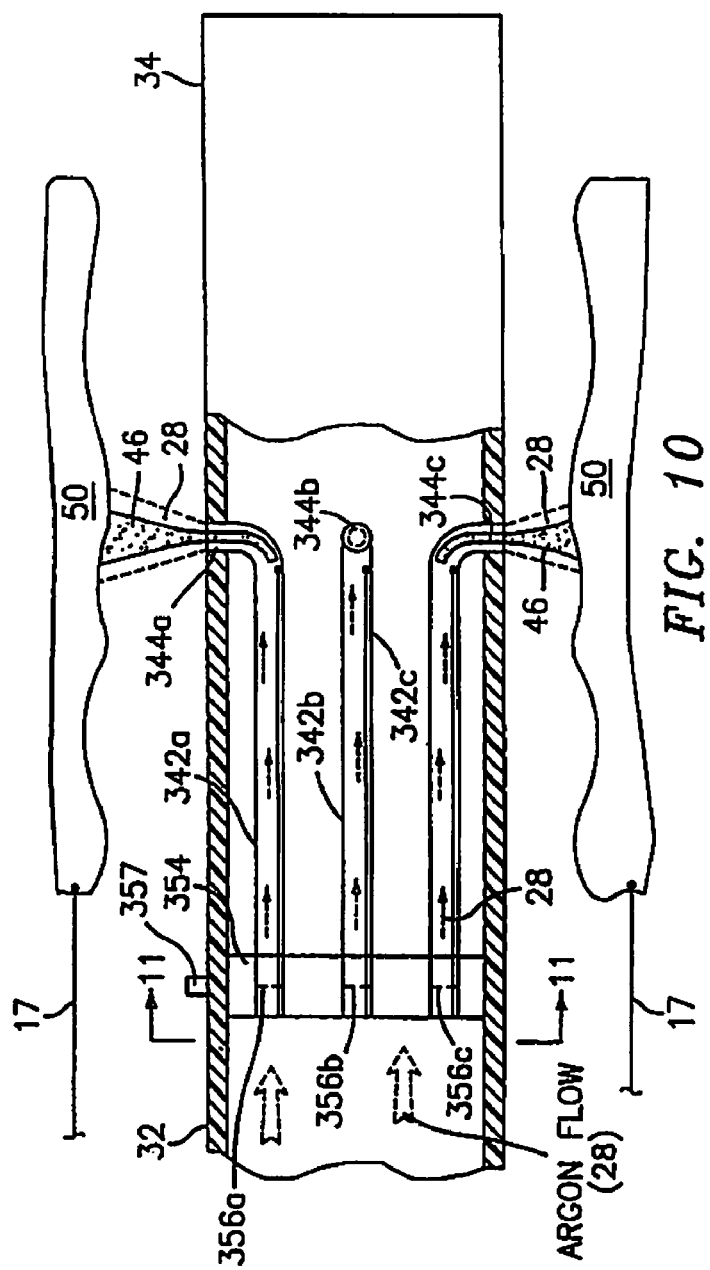
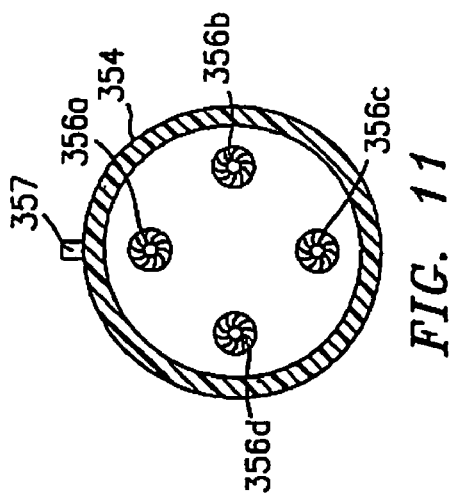
FIG. 10
FIG. 11

MULTI-PORT SIDE-FIRE COAGULATOR

CROSS REFERENCE TO RELATED APPLICATION

This application is a continuation of and claims priority to U.S. application Ser. No. 10/919,614, filed Aug. 17, 2004, which claims priority from U.S. application Ser. No. 10/316,228, filed Dec. 10, 2002 (now U.S. Pat. No. 6,852,112), which claims priority from U.S. application Ser. No. 09/666,954 filed Sep. 20, 2000 (now U.S. Pat. No. 6,616,660), which claims priority from Provisional Application Ser. No. 60/157,718 filed Oct. 5, 1999, each of which are incorporated in their entirety herein by reference.

TECHNICAL FIELD

The present disclosure relates to devices for use with endoscopes and other electrosurgical instruments for coagulating tissue. More particularly, the present disclosure relates to an argon-enhanced electrosurgical device for coagulating tissue which extends through a working channel of an endoscope.

BACKGROUND OF RELATED ART

Devices for arresting blood loss and coagulating tissue are well known in the art. For example, several prior art instruments employ thermic coagulation (heated probes) to arrest bleeding. However, since the probe must come into close contact with the bleeding tissue, the probe may adhere to the eschar during probe removal possibly causing repeat bleeding. Other instruments direct high frequency electric current through the tissue to stop the bleeding. Again, eschar adherence may also be a problem with these instruments. In both types of instruments, the depth of the coagulation is difficult to control.

U.S. Pat. No. 5,207,675 to Canady attempts to resolve certain of the above-noted problems with respect to the prior art by providing a tube-like coagulation instrument in which an inert gas is forced through the instrument and ionized by an electrode prior to the gas exiting the distal end of the instrument towards the bleeding tissue. U.S. Pat. No. 5,720,745 to Farin et al. discloses a coagulation instrument which extends through a working channel of an endoscope and includes an electrode for ionizing a stream of inert gas exiting the distal end of the instrument at a rate of less than about 1 liter/minute. As explained in great detail in the Farin et al. specification, the purpose of discharging the gas at a very low flow rate is to effectively cloud the tissue area and create an inert gas "atmosphere" to gently coagulate the tissue. In both of the above patents, the electrodes are not designed to come into direct contact with the tissue.

However, using these instruments to treat certain more tubular sites, e.g., the esophagus and/or colon, is often difficult, impractical and time consuming and may cause unintended collateral damage to the surrounding tissue. For example, the longitudinally oriented instruments fire the inert gas and the RF energy in an axial direction from its distal end which, in the case of tubular tissue, would be parallel to the bleeding tissue. Thus, focusing the energy transversely at the bleeding tissue may be very difficult using this instrument and may cause collateral tissue damage.

Thus, a need exists for the development of a new and effective instrument for treating certain more tubular tissue and for treating tissue at multiple bleeding sites off axis to the instrument.

SUMMARY

The present disclosure relates to an electrosurgical instrument for coagulating tissue for use in combination with an endoscope which includes an elongated flexible tube having a proximal end and a distal end and a plurality of side-ports located therethrough between the proximal and distal ends. The tube is sufficiently dimensioned to extend through a working channel of an endoscope. An ionizable gas is supplied to the proximal end of the tube and a diffusing member directs the ionizable gas from the proximal end to each of the side-ports towards the tissue. An electrode ionizes the gas prior to the ionizable gas exiting each side-port.

In one embodiment of the present disclosure, the side ports are arranged in a radial manner about the periphery of the tube. In another embodiment, the side-ports are aligned longitudinally along the tube.

A first plenum or baffle having a plurality of apertures located therethrough can be disposed within the tube between the proximal and distal ends. Preferably, the plenum couples to a corresponding plurality of ducts to direct individual amounts of ionizable gas to each of the side-ports. Advantageously, electrodes are disposed within each of the ducts for ionizing the gas prior to the gas exiting the side-ports towards the tissue.

Further, a second plenum, surface or disc can be mounted in close abutment with and proximal to the first plenum. This second plenum includes a plurality of apertures located therethrough. Preferably, the second plenum or disc rotates from a first position in which the apertures of the second plenum and the apertures of the first plenum are aligned to permit the free flow of gas between each of the same, and at least one subsequent position in which less than all of the apertures of the second plenum are aligned with the apertures of the first plenum to permit gas to only flow between the aligned apertures to each corresponding side-port.

BRIEF DESCRIPTION OF THE DRAWINGS

FIG. 2 is an enlarged, side sectional view of one embodiment of the present disclosure showing the ionized gas exiting multiple radially disposed side-ports to simultaneously coagulate tissue at multiple sites;

FIG. 3 is a cross-section of FIG. 2 taken along line 3-3.

FIG. 5A-5D are cross-sectional views of FIG. 4 taken along line 5-5 showing four possible rotatable positions for the second plenum;

FIG. 10 is an enlarged, side sectional view of an alternate embodiment of the present disclosure showing a second plenum having a plurality of shutters located therethrough for selectively regulating the gas flow to the first plenum; and FIG. 11 is a cross-section of FIG. 10 taken along lines 11-11.

DETAILED DESCRIPTION

Figure 1:
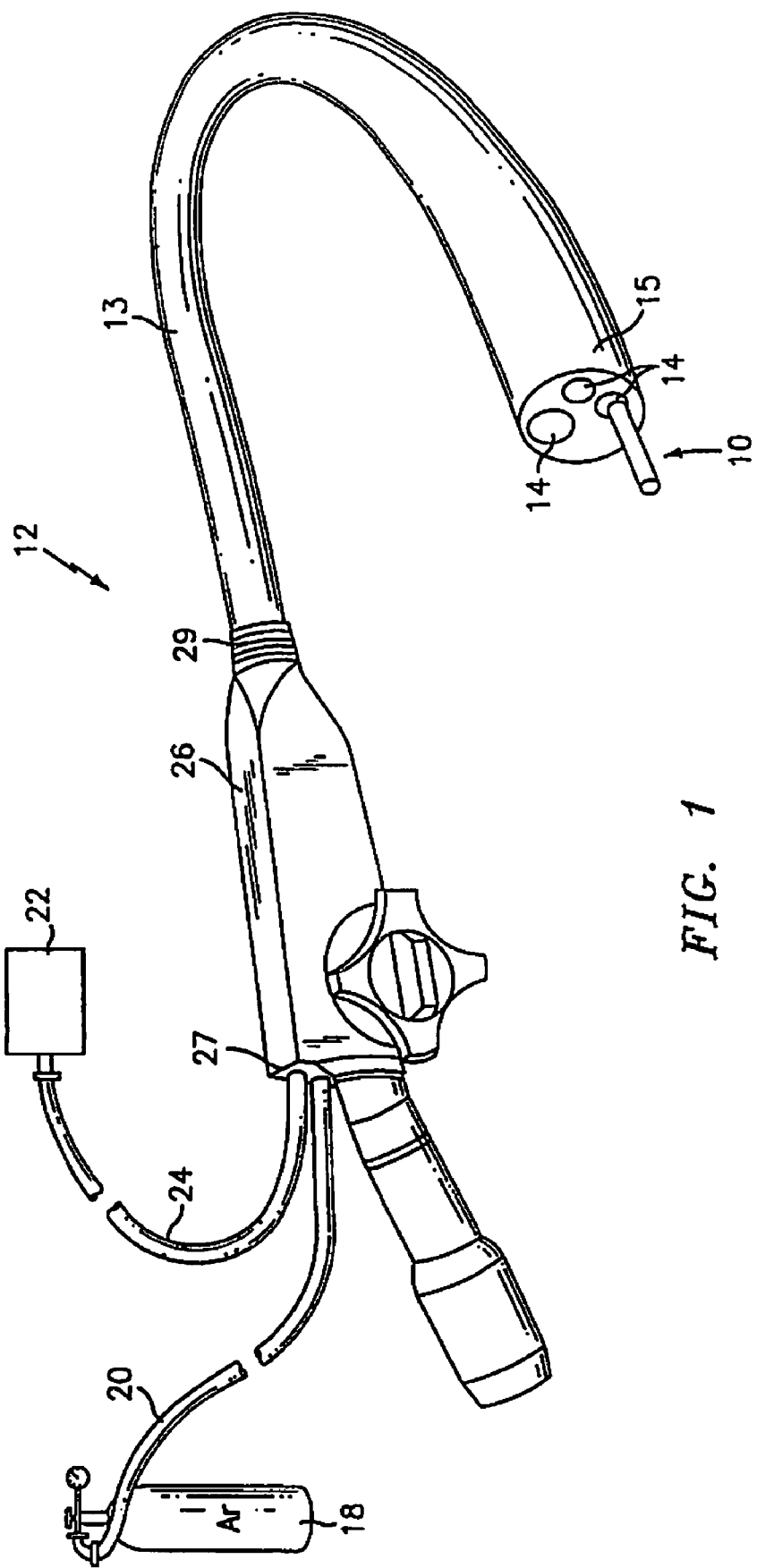
FIG. 1 is a front, perspective view of an electrosurgical instrument shown extending through a working channel of an endoscope.

Referring now to FIG. 1, a multi-port side-fire tissue coagulator, generally identified by reference numeral 10 is shown extending through a working channel of an endoscope 12. Preferably, the multi-port coagulator 10 can be employed with a variety of different endoscopes such as those manufactured by Olympus, Pentax and Fujinon. As such, only the basic operating features of the endoscope 12 which work in combination with the present disclosure need to be described herein.

For example, endoscope 12 includes a handpiece 26 having a proximal end 27 and a distal end 29. Preferably, the proximal end 27 is mechanically coupled to a supply 18 of ionizable gas by way of hose 20 and electrically coupled to an electrosurgical generator 22 by way of cable 24 to supply a source of electrosurgical energy, e.g., high frequency coagulation current, to the endoscope 12. It is envisioned that the electrosurgical generator 22 selectively controls the amount of electrosurgical energy transmitted to an electrode or a plurality of electrodes 48a-48d (see FIG. 2) during a surgical procedure.

As shown in FIG. 1, a long, flexible tubular member 13 having a plurality of working channels 14 located therein is mechanically coupled to the distal end 29 of the handpiece 26. Preferably, at least one of the working channels 14 is sufficiently dimensioned to receive the multi-port coagulator 10 of the present disclosure. Other working channels 14 can be utilized to receive other surgical instruments and accessories such as graspers and biopsy forceps.

Turning now to FIG. 2A which show one embodiment of the multi-port coagulator 10 of the present disclosure which includes an elongated generally flexible tube 30 having a proximal end 32 which is preferably engaged within one of the working channels 14 of the endoscope 12 and a distal end 34 which projects outwardly from the distal end 15 of tube 13. Ionizable gas 28, e.g., argon, is supplied to the proximal end 32 of the coagulator 10 by a gas conduit (not shown) located inside tube 13. Preferably, gas 28 is supplied from source 15 to the coagulator 10 at a selectable, predetermined flow rate.

Advantageously, the flow rate of the gas 28 is selectively adjustable and can easily be regulated depending upon a particular purpose or a particular surgical condition.

As mentioned above, the gas 28 is supplied under pressure to the proximal end 32 of the coagulator 10 and flows generally within the tube 30 in the direction of the arrows. As seen best in FIG. 3, the coagulator also includes a first plenum or baffle 36 having a series of apertures 40a-40d located therethrough for directing the flow of the gas 28 into a corresponding series of ducts or conduits 42a-42d which extend from the first plenum 36 towards the distal end 34.

Figure 4:
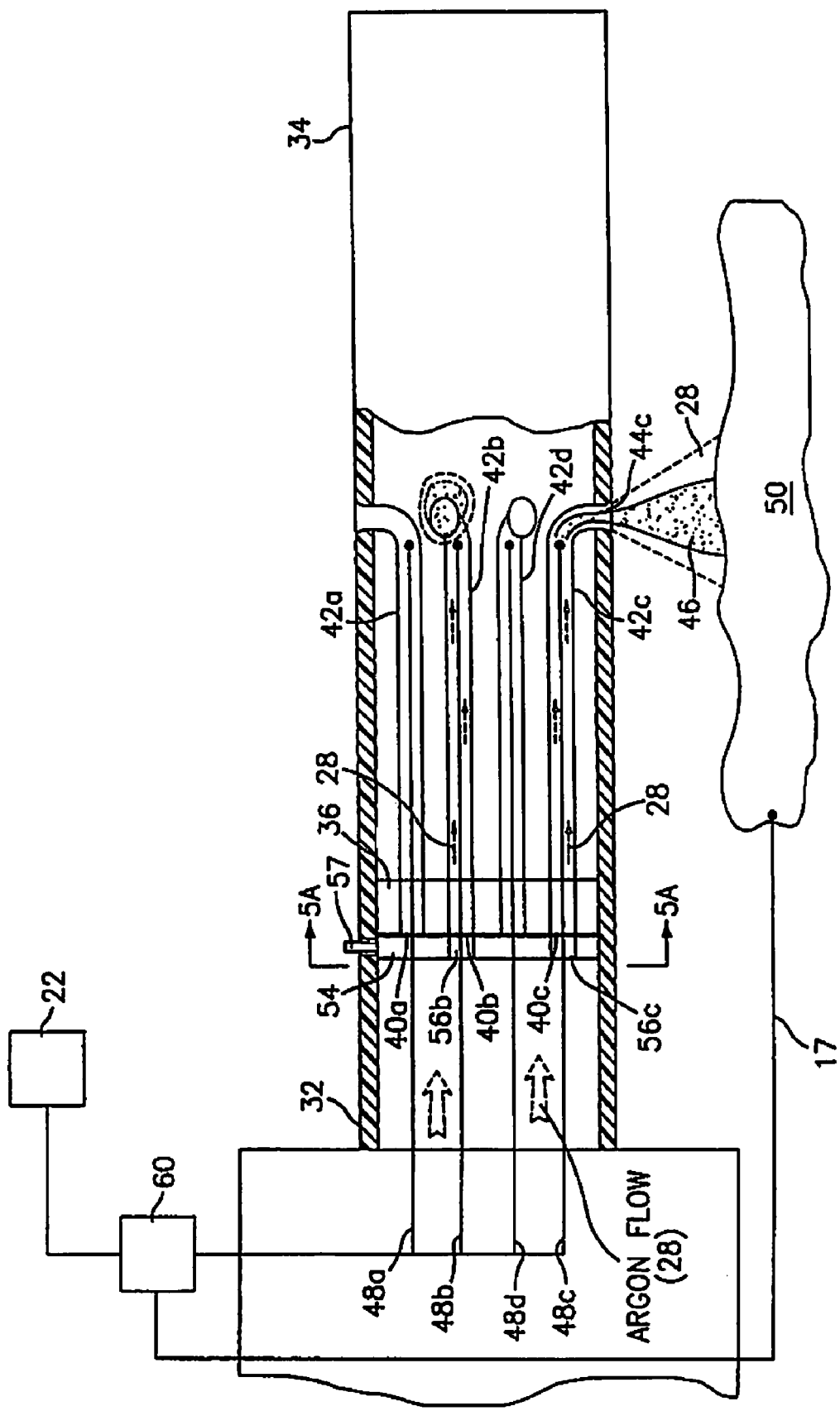
FIG. 4 is an enlarged, side sectional view of an alternate embodiment of the present disclosure showing a rotatable second plenum for regulating gas flow to the first plenum.
Figure 6:
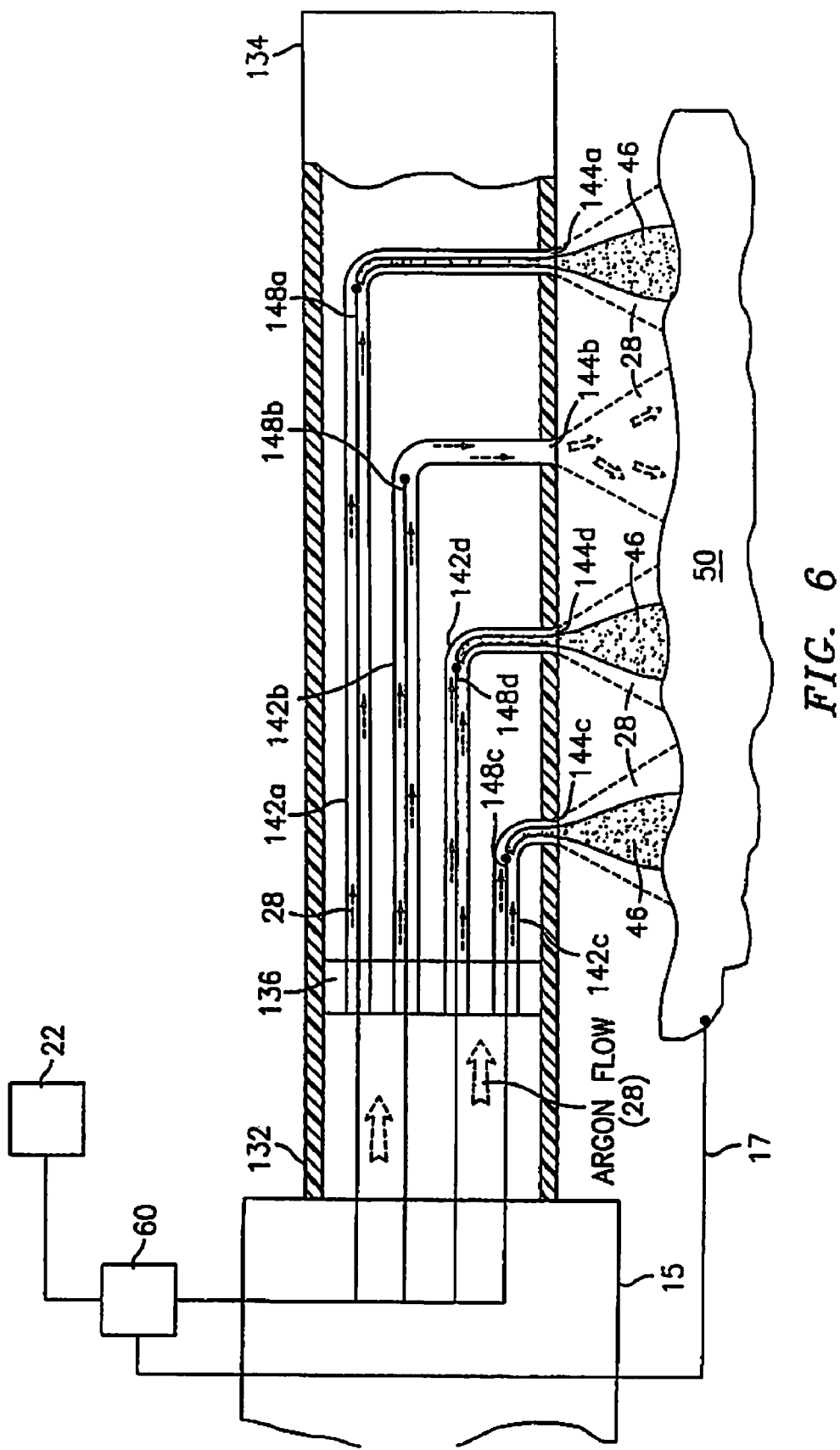
FIG. 6 is an enlarged, side sectional view of an alternate embodiment of the present disclosure showing the ionized gas exiting multiple longitudinally-aligned side-ports to simultaneously coagulate the tissue at multiple longitudinally-disposed bleeding sites.
Figure 9:
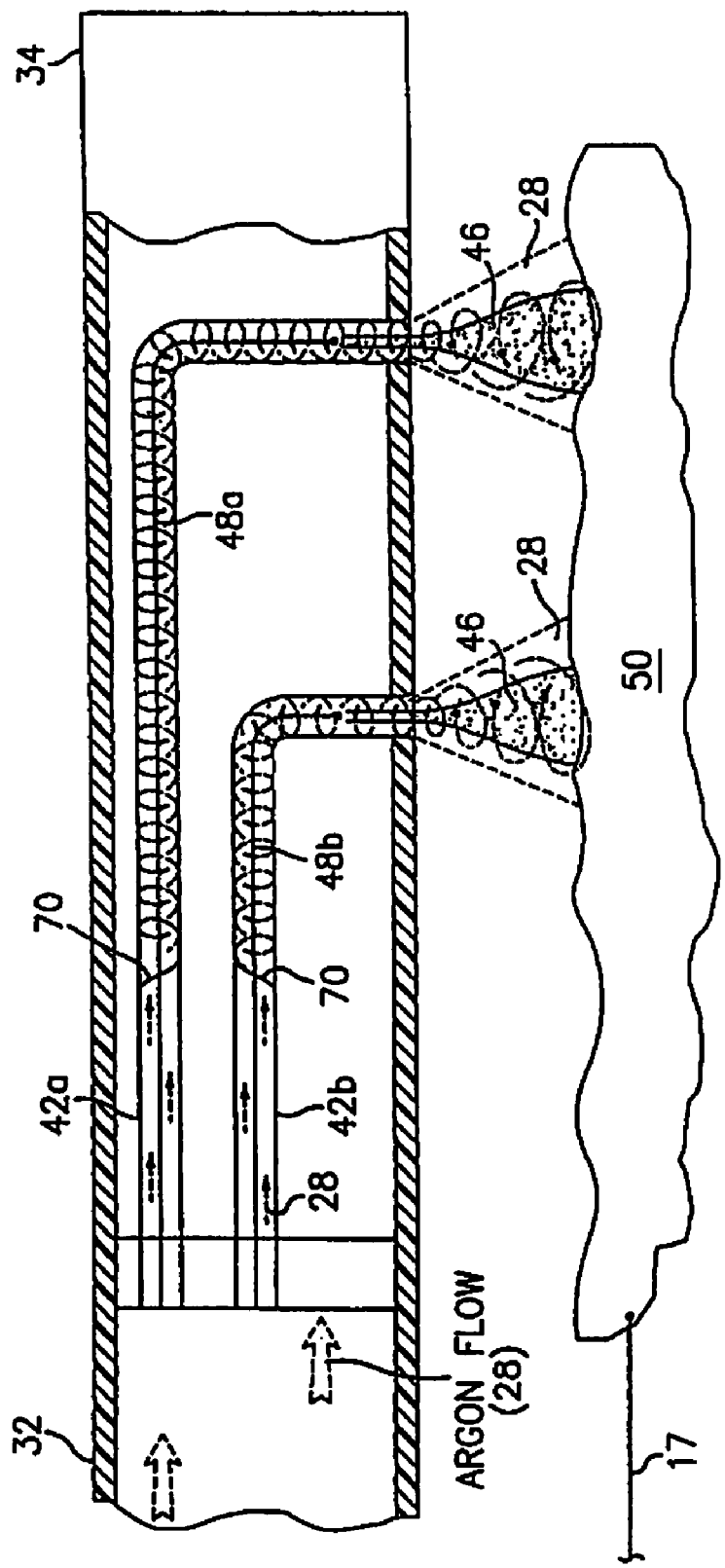
FIG. 9 is an enlarged, side sectional view of an alternate embodiment of the present disclosure showing the gas being conducted through a series of ducts each having a helically-shaped baffle located therein for causing the gas to exit the side ports in a more turbulent manner towards the tissue.

Preferably, each duct 42a-42d leads to a corresponding series of side-ports 44a-44d located at various positions along the tube 30. It is contemplated that the side-ports 44a-44d can be disposed along tube 30 in any one of a number of different configurations and work simultaneously to direct the gas 28 to the surrounding tissue 50. For example, FIGS. 2, 4 and 10 depict the side-ports 44a-44d radially disposed about the periphery of the tube 30 which enable an operator to more effectively coagulate tubular-shaped tissue 50 at multiple bleeding sites. FIGS. 6 and 9 depict the side-ports 44a-44d arranged in a more longitudinally-aligned manner along the outer periphery of the tube 30 which enable the operator to more effectively coagulate bleeding tissue 50 with more longitudinal-type lesions, i.e., tissue lesions which run parallel to the axial direction of endoscope 12, and without causing collateral tissue damage.

Utilizing this instrument, multiple tissue lesions can be treated and coagulated simultaneously. Moreover and as described in detail below, the operator can more effectively adjust the amount and pressure of the gas 28 prior to and/or during the surgical procedure depending upon a particular purpose.

As best seen in FIGS. 2 and 4, each duct 42a-42d preferably includes an electrode 48a-48d, respectively, located therein. The electrodes 48a-48d discharge an electrosurgical current, e.g., radiofrequency (RF), which ionizes a stream of gas 46 prior to the gas 28 exiting each respective side-port 44a-44d towards the tissue 50. The stream of ionized gas 46 conducts the current to the tissue 50 while effectively scattering blood away from the treatment site allowing the tissue 50 to readily coagulate and arrest bleeding.

In one embodiment, the electrodes 48a-48d are connected by way of one or more electrical conduits (not shown) disposed within tubes 30 and 13 which are ultimately connected to electrosurgical generator 22. Preferably, the electrodes 48a-48d are ring or pin-type electrodes and are spaced from each respective side-port 44a-44d such that the electrodes 48a-48d cannot come into contact with the tissue 50 during the surgical procedure. A patient return electrode or pad 17 can also be electrically coupled to the electrosurgical generator 22 or, as discussed below, an electrode control mechanism 60 which allows the operator to selectively adjust the amount of current flowing through each electrode 48a-48d. For example, the operator can selectively activate and/or deactivate any combination of electrodes 48a-48d depending upon a particular purpose, e.g., FIG. 6 shows only three electrodes, namely, 148a, 148c and 148d, being activated to coagulate tissue 50.

FIGS. 4 and 5A-5D show an alternate embodiment of the present disclosure which includes a second baffle or closure disc 54 disposed proximal to and in close abutment with plenum 36. Preferably, closure disc 54 includes a plurality of pre-aligned apertures 56a-56f located therethrough and is rotatably mounted within tube 30 such that the disc 54 is rotatable from a first position which permits the gas 28 to flow freely therethrough and to plenum 36, to at least one subsequent position which limits the flow of gas 28 to plenum 36.

For example, when disc 54 is rotated such that tab 57 is oriented at the 12:00 position (FIG. 6A), gas 28 is free to flow through apertures 56a-56d to corresponding apertures 40a-40d of plenum 36. However, when tab 57 is rotated to the 10:30 position (FIG. 5B), gas 28 can only flow through apertures 56e and 56f at the 12:00 and 6:00 positions to apertures 40a and 40c of plenum 36 and the other apertures 40b and 40d of plenum 36 are effectively sealed. Again, when tab 57 is rotated to the 9:00 position (FIG. 5C), gas is permitted to freely flow through apertures 56a-56d to apertures 40a-40d of plenum 36, but when tab 57 is rotated to the 7:30 position (FIG. 5D), gas can only flow through apertures 56e and 56f at the 9:00 and 3:00 positions to apertures 40b and 40d of plenum 36. It is envisioned that disc 54 can be manufactured with any combination or arrangement of apertures to limit and/or control the flow of gas 28 to plenum 36.

In another embodiment of the present disclosure, the disc 54 may include a plurality of pre-sized apertures 56a-56f which regulate the amount of gas 28 flowing to the first plenum 36. Advantageously, disc 54 is selectively interchangeable and/or selectively sizable to permit more or less gas 28 to flow between apertures 56a-56f and 40a-40d and/or to limit the gas 28 flow to any one aperture, e.g., 40a.

Figure 7:
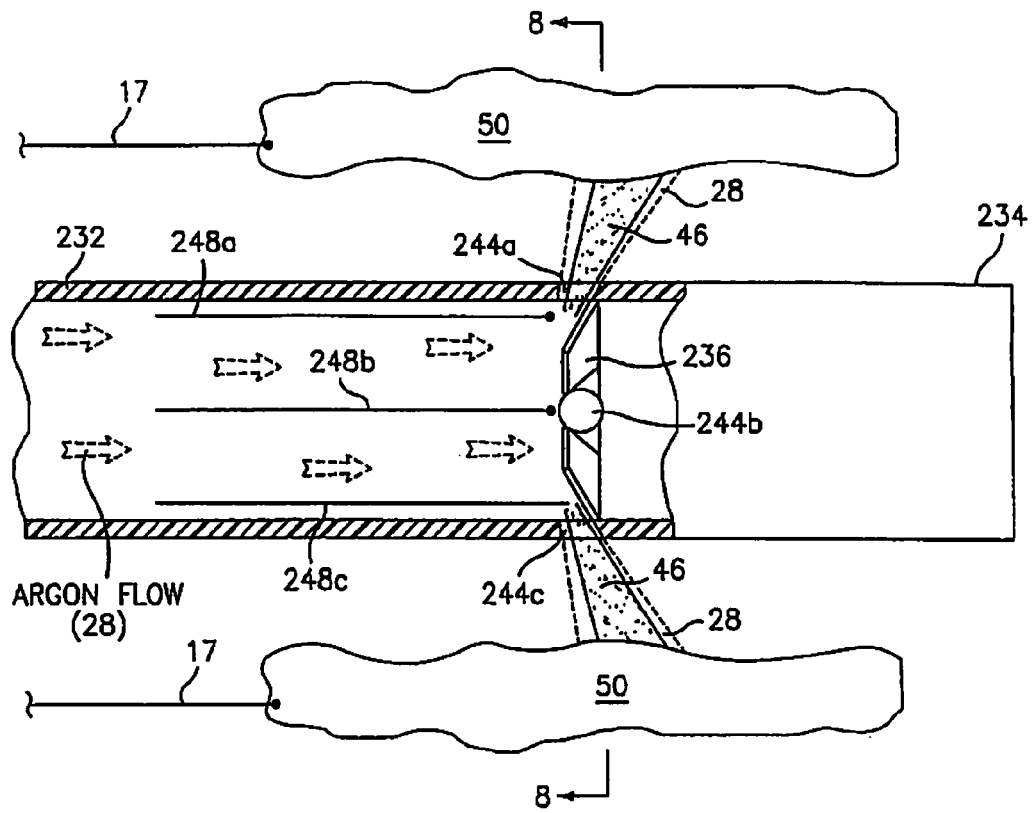
FIG. 7 is an enlarged, side sectional view of an alternate embodiment of the present disclosure showing the gas being directed to multiple side-ports by way of a multi-partitioned wedge-like damper.
Figure 8:
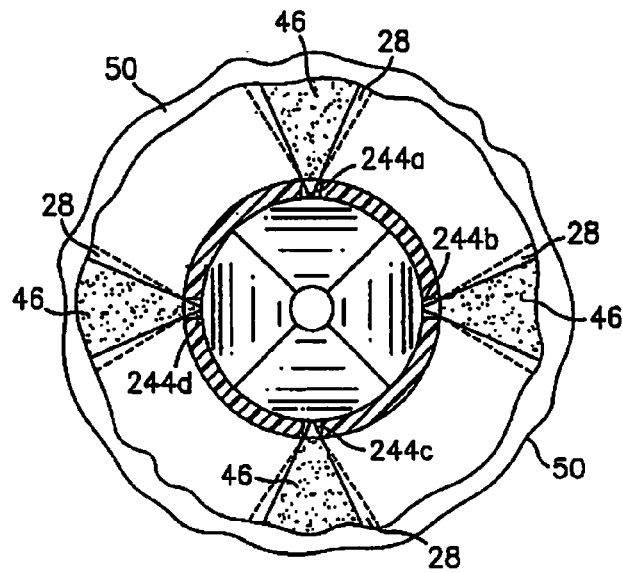
FIG. 8 is a cross sectional view of the FIG. 7 embodiment taken along lines 8-8.

FIGS. 7 and 8 show an alternate embodiment of the first plenum 36 of FIGS. 2-6 and include a frustoconically-shaped quadfurcated (four distinct partitions) wedge 236 which directs the flow of gas 28 to four side-ports 244a-244d preferably located at the 12:00, 3:00, 6:00 and 9:00 positions, respectively. A series of electrodes 248a-248d (248d not shown) are each disposed proximate to each respective side-port 244a-244d to ionize the gas 28 prior to the gas 28 exiting each side-port 244a-244d. Preferably, the electrodes 248a-248d are disposed distant from the side-ports such that the electrodes 248a-248d cannot contact the tissue 50 which, as mentioned above, can have a traumatic effect on the tissue 50.

As shown best in FIG. 8, this embodiment of the disclosure is particularly useful for simultaneously coagulating tissue 50 at multiple treatment sites which are radially disposed from one another. Moreover, an operator can simply rotate the coagulator 10 slowly to effectively and readily coagulate the entire tissue area surrounding the side-ports 244a-244d.

Although, FIGS. 7 and 8 show wedge 236 as being quadfurcated to direct the gas 28 to four corresponding side-ports 244a-244d, in some cases it may be preferable to provide a wedge which is only trifurcated and directs gas 28 to three corresponding side-ports, e.g., 244a-244c. In other cases it may be preferable to provide a wedge 236 which includes more or less partitions for directing gas 28 to a corresponding number of side-ports.

FIG. 9 shows yet another alternate embodiment of the present disclosure wherein the gas 28 is caused to flow in a more turbulent manner through each respective duct 42a, 42b. Many devices may be employed to cause the gas 28 to flow more or less turbulently through the ducts 42a, 42b. For example, FIG. 9 includes a generally helically-shaped baffle 70 which causes gas 28 to swirl within ducts 46a, 46b prior to the gas 28 exiting side-ports 44a, 44b.

FIGS. 10 and 11 show an alternate embodiment of the closure disc 354. In particular, disc 354 is preferably disposed within plenum 36 and includes a plurality of shutters 356a-356d which can be selectively opened and closed to regulate the amount of gas 28 flowing through corresponding apertures 40a-40d of plenum 36. One or more tabs 357 can be employed to selectively control the shutters 356a-356d either individually or in unison.

From the foregoing and with reference to the various figure drawings, those skilled in the art will appreciate that not only can the coagulator 10 of the present disclosure be used to arrest bleeding tissue, but the present disclosure can also be employed for desiccating the surface tissue, eradicating cysts, forming eschars on tumors or thermally marking tissue. Those skilled in the art will also appreciate that certain modifications can also be made to the present disclosure without departing from the scope of the present disclosure. For example, while the location of the various side-ports have been shown radially and longitudinally disposed about the periphery of the tube 30, in some cases it may be preferable to position the side-ports about tube 30 differently depending upon a particular purpose, e.g., helically, in longitudinal or radial pairs and/or radially and longitudinally offset from one another.

There have been described and illustrated herein several embodiments of a multi-port coagulator for arresting bleeding and performing other surgical procedures. While particular embodiments of the disclosure have been described, it is not intended that the disclosure be limited thereto, as it is intended that the disclosure be as broad in scope as the art will allow and that the specification be read likewise. Therefore, the above description should not be construed as limiting, but merely as exemplifications of preferred embodiments. Those skilled in the art will envision other modifications within the scope and spirit of the claims appended hereto.

What is claimed is:

1. An electrosurgical apparatus for coagulating tissue, comprising:
    an elongated flexible tube having a proximal end and a distal end, the tube comprising a plurality of side-ports which are disposed therethrough between the proximal and distal ends;
    a diffusing member for directing ionizable gas from the proximal end of the tube through each of said side-ports and towards the tissue, the diffusing member including a first plenum disposed within the tube between the proximal and distal ends having a plurality of apertures defined therethrough, at least one of the apertures including a corresponding baffle disposed therein operably configured to cause the ionizable gas to exit the corresponding side-port with predetermined flow characteristics; and
    a corresponding plurality of electrodes disposed proximate each side port operable to ionize the ionizable gas prior to the ionizable gas exiting the side-ports.

2. An electrosurgical apparatus according to claim 1, further including a corresponding plurality of ducts coupled between each of the apertures and each of the side-ports, each duct configured to direct an amount of the ionizable gas to a corresponding side port.

3. An electrosurgical instrument according to claim 1, wherein the baffle is helically-shaped.

4. An electrosurgical instrument according to claim 1, further including a regulator that allows a user to selectively adjust the amount of electrical current flowing to each corresponding electrode after activation.

5. An electrosurgical instrument according to claim 4, wherein the regulator includes at least one control switch that regulates the electrical current to each corresponding electrode.

6. An electrosurgical instrument according to claim 1, wherein the side-ports are arranged in a radial manner about the elongated tube.

7. An electrosurgical instrument according to claim 1, wherein the side-ports are aligned longitudinally along the elongated tube.

8. An electrosurgical instrument according to claim 1, wherein the diffusing member includes a second plenum that is selectively mounted within the elongated tube in close abutment with and proximal to the first plenum and includes a plurality of apertures therethrough.

9. An electrosurgical instrument according to claim 8, wherein the plurality of apertures of the second plenum are pre-sized to regulate the flow of ionizable gas through each of the plurality of apertures to each of the corresponding apertures of the first plenum.

10. An electrosurgical instrument according to claim 8, wherein the second plenum is selectively rotatable from a first position in which the apertures of the second plenum and the apertures of the first plenum are aligned to permit the ionizable gas to flow therebetween in a generally unrestricted manner to at least one subsequent position in which less than the plurality of apertures of the second plenum are aligned with the apertures of the first plenum to restrict the flow of ionizable gas between plenums.

* * * * *

UNITED STATES PATENT AND TRADEMARK OFFICE
CERTIFICATE OF CORRECTION

| | | |
|---|---|---|
| PATENT NO. | : 7,927,330 B2 | Page 1 of 1 |
| APPLICATION NO. | : 12/047864 | |
| DATED | : April 19, 2011 | |
| INVENTOR(S) | : Platt | |

It is certified that error appears in the above-identified patent and that said Letters Patent is hereby corrected as shown below:

Title Page,
In the "Related U.S. Application Data" item (63), the listing of applications should read, "Continuation of application No. 10/919,614, filed on Aug. 17, 2004, now Pat. No. 7,955,330, which is a continuation of application No. 10/316,228, filed on December 10, 2002, now Pat. No. 6,852,112, which is continuation of application No. 09/666,954, filed on September 20, 2000, now Pat. No. 6,616,660, which claims benefit of provisional application No. 60/157,718, filed on October 5, 1999."

Signed and Sealed this
Fourth Day of October, 2011

David J. Kappos
*Director of the United States Patent and Trademark Office*